(12) United States Patent
Fecteau et al.

(10) Patent No.: US 6,254,236 B1
(45) Date of Patent: *Jul. 3, 2001

(54) PARABOLIC AND HYPERBOLIC ASPHERIC EYEWEAR

(75) Inventors: Keith Fecteau, Wilbraham, MA (US); James Hall, Lincoln, RI (US); Raoul Desy, Sturbridge; John Salce, Auburn, both of MA (US); David M. Hasenauer, Monrovia, CA (US)

(73) Assignee: Cabot Safety Intermediate Corporation, Southbridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/369,115

(22) Filed: Aug. 5, 1999

Related U.S. Application Data

(63) Continuation-in-part of application No. 09/149,629, filed on Sep. 8, 1998, now Pat. No. 6,019,469, which is a continuation of application No. 08/806,832, filed on Feb. 26, 1997, now Pat. No. 5,825,455, which is a continuation-in-part of application No. 08/641,901, filed on May 2, 1996, now abandoned.

(51) Int. Cl.[7] .................................................... G02C 7/02

(52) U.S. Cl. .............................................. 351/159; 351/41
(58) Field of Search .............................. 351/159, 160 R, 351/160 H, 41, 43–44; 2/6.3, 425–426

(56) References Cited

U.S. PATENT DOCUMENTS

| | | | |
|---|---|---|---|
| 3,283,446 | * 11/1966 | Feinbloom | 351/177 |
| 4,674,851 | 6/1987 | Jannard | 351/47 |
| 4,741,611 | 5/1988 | Burns | 351/44 |
| 4,859,048 | 8/1989 | Jannard | 351/159 |
| 4,867,550 | 9/1989 | Jannard | 351/47 |
| 4,978,182 | 12/1990 | Tedesco | 359/15 |
| 5,032,017 | 7/1991 | Bolle et al. | 351/116 |
| 5,050,981 | * 9/1991 | Roffman | 351/177 |
| 5,204,700 | * 4/1993 | Sansalone | 351/41 |
| 5,381,192 | 1/1995 | Canavan et al. | 351/118 |
| 5,604,547 | * 2/1997 | Davis et al. | 351/159 |
| 5,648,832 | * 7/1997 | Houston et al. | 351/159 |
| 5,825,455 | * 10/1998 | Fecteau et al. | 351/159 |
| 6,019,469 | * 2/2000 | Fecteau et al. | 351/159 |

* cited by examiner

Primary Examiner—Jordan M. Schwartz
(74) Attorney, Agent, or Firm—Cantor Colburn LLP

(57) ABSTRACT

Piano lenses and associated eyewear incorporating parabolic and hyperbolic arcs are provided which are particularly useful in safety and recreational applications.

48 Claims, 8 Drawing Sheets

R1 = R2

R1 = R2

R1 ≠ R2

R1 ≠ R2

PARABOLIC AND HYPERBOLIC ASPHERIC EYEWEAR

CROSS-REFERENCE TO RELATED APPLICATIONS

This is a continuation-in-part of application Ser. No. 09/149,629 filed Sep. 8, 1998 (now U.S. Pat. No. 6,019,469, which is a continuation of application Ser. No. 08/806,832 filed Feb. 26, 1997, (now U.S. Pat. No. 5,825,455), which is a continuation-in-part of application Ser. No. 08/641,901 filed May 2, 1996, now abandoned.

FIELD OF THE INVENTION

This invention relates generally to eyewear. More particularly, this invention relates to plano eyewear for use in safety and recreational (i.e., sports) applications. Examples of suitable eyewear applications include spectacles, goggles, faceshields, respirator lenses, visors, helmets and the like.

BACKGROUND OF THE INVENTION

Traditional plano (that is, non corrective or zero power) eyewear is constructed using lenses which are flat or spherical. A spherical lens surface is obtained when a circle is rotated about its diameter. Prior art FIGS. 1 and 2 depict a conventional spherical lens where FIG. 1 is a unitary spherical lens and FIG. 2 is a bispheric lens. As shown in FIGS. 1 and 2, the lens surface is a segment of a sphere such that a cross-section taken in any meridian through the center of the sphere will reveal an arc of constant radius R.

More recently, in an effort to improve protection to the wearer's eyes, attempts have been made to allow the lenses to curve along more of the wearer's face, that is, to achieve a larger wrap depth so as to protect the sides of the eyes. This has been accomplished using toric and cylindrical surfaces, all of which have been based on circular or spherical geometries. A circular toric surface is obtained when a circle is rotated about an axis which is located in the same plane as the circle, but at some distance from the diameter of the circle. The resulting three dimensional shape is a donut or toroid and the toric lens consists of a section of that formed donut. Prior art FIGS. 3 and 4 depict toric lenses where FIG. 3 is a unitary circular toric lens and FIG. 4 is a bi-toric lens. In both FIGS. 3 and 4, the resulting lens has a constant radius of curvature in the horizontal meridian of $R_2$ and a constant radius of curvature in the vertical meridian of $R_1$ Prior art examples of toric plano eyewear is disclosed in U.S. Pat. No. 4,867,550 to Jannard and U.S. Pat. No. 4,741,611 to Burns.

A cylinder is obtained when a circle is rotated about an axis which is located an infinite distance from the diameter of the circle. Prior art FIG. 5 depicts a unitary cylindrical lens used in eyewear. The cylinder can also be described as the surface obtained when a circle is extruded in a direction perpendicular to the plane of the circle. As shown in FIG. 5, the resulting lens has a constant radius of curvature $R_1$ in the horizontal meridian and a vertical axis radius of curvature $R_2$ equal to (which is essentially a straight line). Prior art examples of cylindrical plano eyewear are disclosed in U.S. Pat. Nos. 4,674,851 and 4,859,048 to Jannard.

As mentioned, all four of the aforementioned lens surfaces (flat, spherical, toric and cylindrical) are based on circular or spherical geometries. Several favorable advantages resulting from the use of such geometries are that the optical performance is easily predictable and the lens surfaces lend themselves easily to manufacture including mold production and lap polishing.

However, the foregoing conventional lens surfaces also suffer from certain serious drawbacks and deficiencies. For example, when spherical, toric or cylindrical lenses are used in piano safety eyewear, it is almost always necessary to have a separate sideshield for lateral protection of the eye. In some commercial designs, the sideshield is a separate component which is attached to, or integrally part of, the temple. In other commercial designs, the sideshield is integrally molded or formed into the lens. In the latter case there is an obvious, visible line of demarcation between the lens, and what is considered to be the sideshield. An example in the prior art of the requirements for such sideshields (either as a separate component or as an integrally molded feature) is described in U.S. Pat. No. 5,381,192 and shown in FIG. 6.

Although lenses based on circular and spherical geometries are easier to produce and their optical properties, easier to predict, design flexibility is limited because the radii in the horizontal and vertical axes are constant. Attempts have been made to design unitary lenses having integrally molded sideshields and no visible line of demarcation between the lens and the sideshield area. However, such lenses (which are made with spherical, cylindrical or circular toric surfaces) will not have sufficient wrap around the sides of the eyes to meet safety standards for lateral protection without being cosmetically and/or functionally unappealing. In order to achieve sufficient wrap, the spectacles have a tendency to take on a "bug-eyed" appearance. The "bug-eyed" appearance can be minimized by utilizing flatter curves, but a flatter curve does not wrap sufficiently close to the temple area. The "bug-eyed" appearance can be somewhat minimized by producing a circular toric. A circular toric lens can be flatter in the vertical meridian but still remains steep in the horizontal meridian. In order to achieve zero power, and to have lens edge thicknesses which will meet safety product impact requirements, and to have sufficient wrap without a separate sideshield, the lens center thickness tends to be relatively high, making the lens heavy and therefore less desirable. An examples of a prior art lens of this type is U.S. Pat. No. 5,032,017 to Bolle et al.

Still another lens surface which provides sufficient wrap but nevertheless maintains an unacceptably large "bug-eyed" appearance for many applications is disclosed in U.S. Pat. No. 4,978,182 to Tedesco. In this latter patent, an ellipse is rotated about its major axis to form an ellipsoid. A section of this ellipsoid is then used to form an eye shield. However, the resultant ellipsoidal lens surface protrudes substantially from the wearer's face and therefore suffers from the same "bug-eyed" appearance as does conventional spherical lens surfaces.

SUMMARY OF THE INVENTION

The above-discussed and other problems and deficiencies of the prior art are overcome or alleviated by the novel plano lens and eyewear incorporating such lens of the present invention. In accordance with the present invention, a plano lens comprises a first surface curvature which is created by rotating an aspheric shape about an axis which is offset from an axis of the aspheric shape.

In a first preferred embodiment, the shape is an ellipse or at least is an aspheric shape having an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse. In a more preferred embodiment, the axis of rotation is coplanar with the ellipse. The resulting surface of this preferred lens configuration will have a cross-section in a first axis which is a segment of an ellipse, and a cross-section in a second axis (perpendicular to the first axis) which is a segment of a circle. A significant feature of the preferred front lens configuration is that the surface generated is rotationally symmetric.

It is preferable to orient the ellipse in the horizontal axis relative to the eye. The changing radius of curvature from relatively flat to progressively steeper in the horizontal meridian allows the lens to sufficiently wrap around the temple area. One large ellipse can be used to produce continuous lens wrapping around both temples, or separate ellipses can be used, one for each eye connected by a center bar, to make a one piece dual lens for a spectacle whereby each lens provides wrap for one of the wearer's temples.

In second preferred embodiment, the shape of the plano lens is a parabola or at least is an aspheric shape having a parabolic arc. This parabolic arc is rotated about an axis spaced (offset) some distance from a given line. In a more preferred embodiment, the parabola is rotated about an axis which intersects a line of symmetry of the parabola, at an angle. In a more preferred embodiment, the axis of rotation is coplanar with the parabola. The resulting surface of this preferred lens configuration will have a cross-section in a first axis which is a segment of a parabola, and a cross-section in a second (perpendicular to the first axes) which is a segment of a circle. If the offset axis is infinitely distanced from the axis of the parabola, the cross-section in such second axis will be a straight line. A feature of the preferred front lens configuration is that the surface generated is rotationally symmetric.

It is preferable to orient the parabola in the horizontal axis relative to the eye. The changing radius of curvature from relatively flat to progressively steeper in the horizontal meridian allows the lens to sufficiently wrap around the temple area. One parabola can be used to produce continuous lens wrapping around both temples, or separate parabolas can be used, one for each eye connected by a center bar, to make a one piece dual lens for a spectacle whereby each lens provides wrap for one of the wearer's temples.

In a third preferred embodiment, the shape of the plano lens is a hyperbola or at least is an aspheric shape having a hyperbolic arc. This hyperbolic arc is rotated about an axis spaced (offset) some distance from a given line. In a more preferred embodiment, the hyperbola is rotated about an axis which intersects a line of symmetry of the hyperbola at an angle. In a more preferred embodiment, the axis of rotation is coplanar with the hyperbola. The resulting surface of this preferred lens configuration will have a cross-section in a first axis which is a segment of a hyperbola, and a cross section in a second axis (perpendicular to the first axis) which is a segment of a circle. If the offset axis is infinitely distanced from the axis of the hyperbola, the cross-section in such second axis will be a straight line. A feature of the preferred front lens configuration is that the surface generated is rotationally symmetric.

It is preferable to orient the hyperbola in the horizontal axis relative to the eye. The changing radius of curvature from relatively flat to progressively steeper in the horizontal meridian allows the lens to sufficiently wrap around the temple area. One large hyperbola can be used to produce continuous lenses wrapping around both temples, or separate hyperbolas can be used, one for each eye connected by a center bar, to make a one piece dual lens for a spectacle whereby each lens provides wrap for one of the wearer's temples.

While preferably the front or outer lens surface of the parabolic and hyperbolic embodiments will have the aspheric configuration described above, the back or inner lens surface will have a different shape which, together with the front lens surface, will result in a plano, substantially plano or zero power optical design. It will be appreciated that by "zero power" or plano, it is meant that the optics provide no substantial visually discernable correction to the human eye. As is well known to those in the art, spectacles are often designated as "zero power" despite providing some small, visually non-discernable correction such as, for example +0.125 to −0.250.

The novel aspheric plano lens configuration of the present invention provides many features and advantages, particularly when compared to prior art flat, spherical, cylindrical and toric plano lenses. First, the lens of this invention will have a high degree of wrap which will obviate the need for separate or integrally formed side shields. Indeed, the wrap is so extensive that the eyewear of this invention will meet the current safety standards of major geographical markets and market segments, again without the need for sideshields. In addition, the lens of this invention will have less of a "bug-eyed" appearance than known spherical or circular toric lens configurations while maintaining substantial wrap. Still another important feature of this invention is that the novel aspheric piano lens will have a lower center thickness than comparable conventional spherical, toric or cylindrical plano lenses and as a result, the eyewear of this invention will be substantially more lightweight.

The novel plano lens and associated eyewear is thus cosmetically pleasing, low weight, provides a high degree of lateral protection due to its high wrap, requires no sideshields, permits a thinner lens, exhibits no "bug-eyed" appearance and provides excellent protection for safety and recreational use. As a result of the foregoing, the plano lens of this invention finds excellent utility as protective lenses in the safety, recreation, or sports eyewear fields.

The above-discussed and other features and advantages of the present invention will be appreciated and understood by those skilled in the art from the following detailed description and drawings.

BRIEF DESCRIPTION OF THE DRAWINGS

Referring now to the FIGURES, wherein like elements are numbered alike in the several FIGURES.

DESCRIPTION OF THE PREFERRED EMBODIMENT

In accordance with the present invention, an aspheric piano lens is provided preferably for use in conjunction with eyewear for the safety and recreational fields. The front surface of the aspheric piano lens of the present invention is created by rotating an aspheric shape (such as an ellipse, parabola or hyperbola) about an axis which is offset from and preferably coplanar with an axis of the aspheric shape. Thus, the surface generated is rotationally symmetrical and is aspheric. A section of the three dimensional shape formed by this symmetric rotation is then utilized as a plano lens.

The details of the aspheric piano lens of the present invention which is formed by off-axis rotation of an ellipse is disclosed in U.S. Pat. No. 5,825,455 to Fecteau et al, which is assigned to the assignee hereof, all of the contents of which are incorporated herein by reference.

Figure 1:
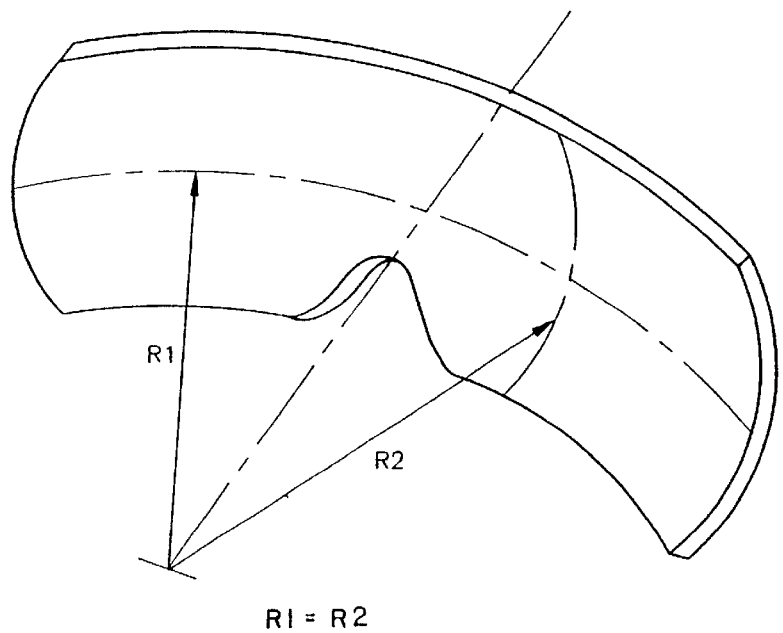
FIGS. 1 and 2 are perspective views of unitary spherical and bi-spheric lenses, respectively, in accordance with the prior art.
Figure 2:
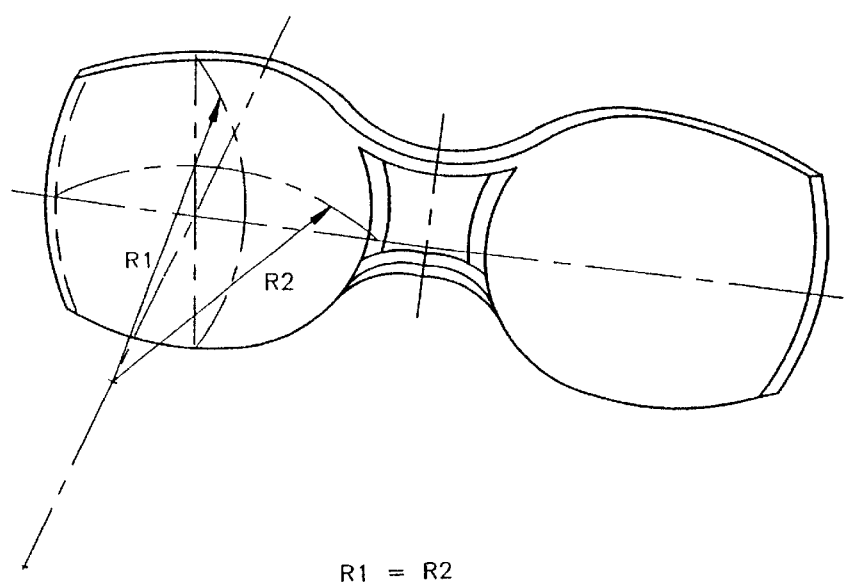
Figure 3:
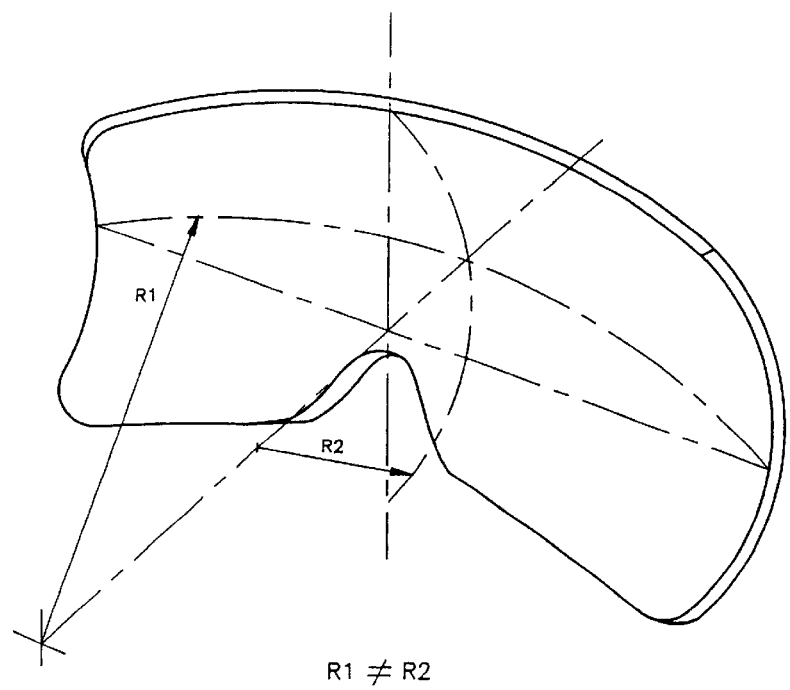
FIGS. 3 and 4 are perspective views of unitary circular toric and bi-toric lenses, respectively, in accordance with the prior art.
Figure 4:
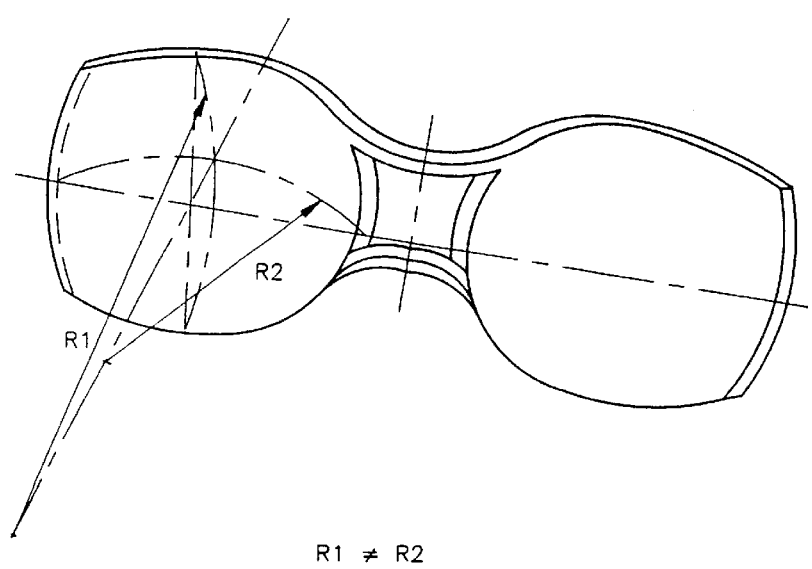
Figure 5:
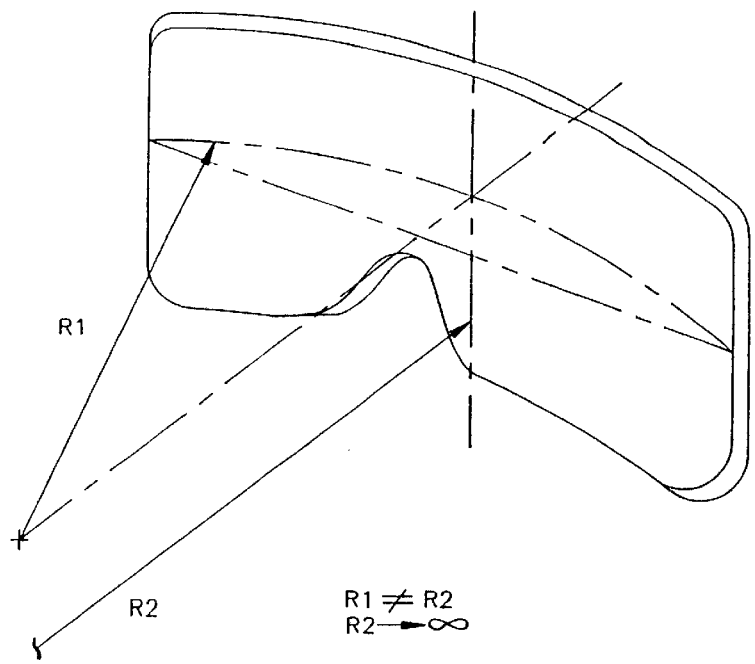
FIG. 5 is a perspective view of a unitary cylindrical lens in accordance with the prior art.
Figure 6:
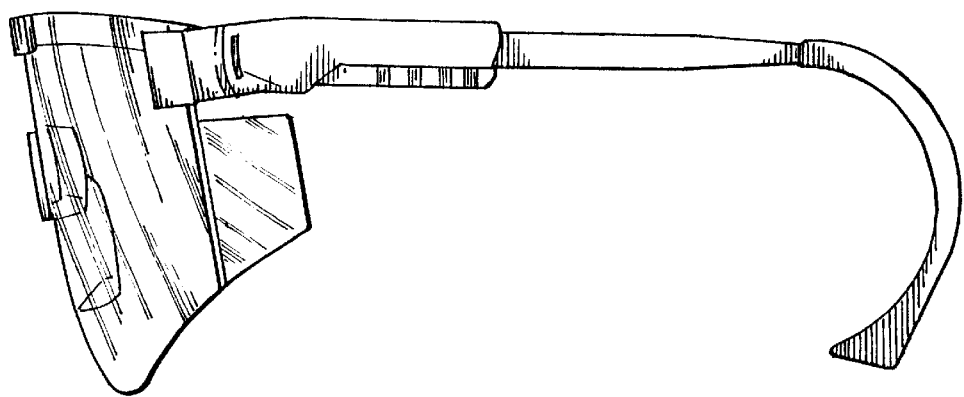
FIG. 6 is a side elevation view of a prior art protective spectacle with integrally molded sideshields.
Figure 7:
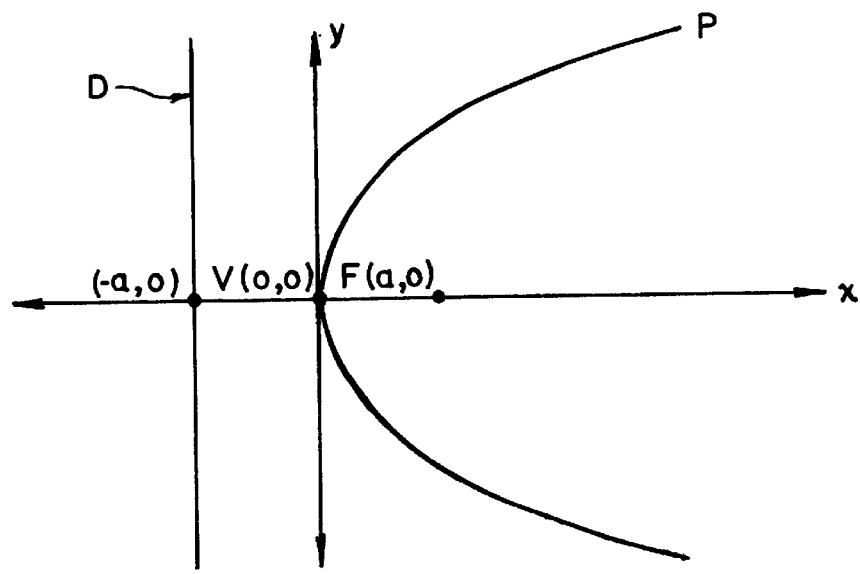
FIGS. 7 and 8 are diagrammatic views depicting the geometry of a parabola and hyperbola, respectively.

Referring to FIG. 7, a parabola P is shown, which is defined as the set of all points in a plane equidistant from a fixed point (the focus "F") and a fixed line (the directrix "D"). The equation of the parabola in FIG. 7 is:

$$y^2 = 4ax$$

where "a" is the x coordinate of the point "F" relative to the vertex "V" of the parabola, and "–a" is the x coordinate for the directrix "D". The parabola is symmetric about the x axis, because both positive and negative values for y will yield the same value for x.

Figure 8:
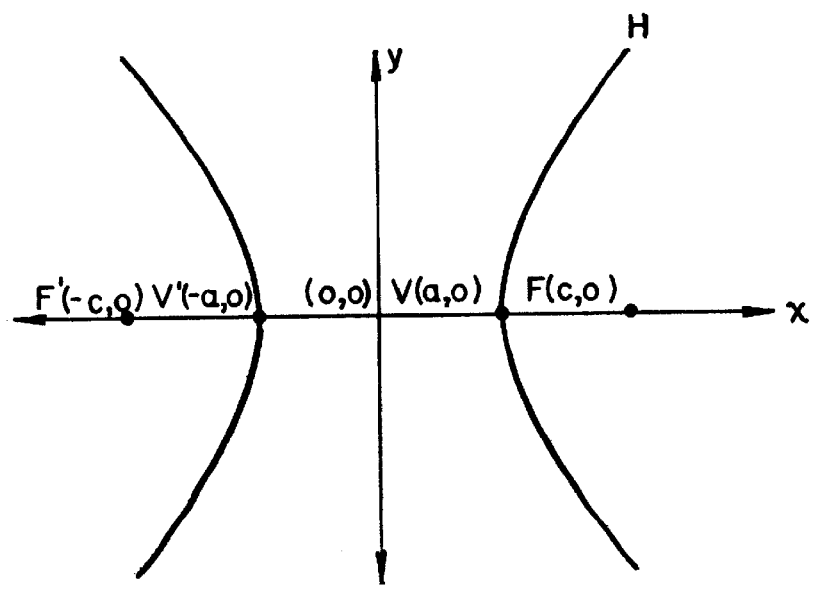
Figure 15:
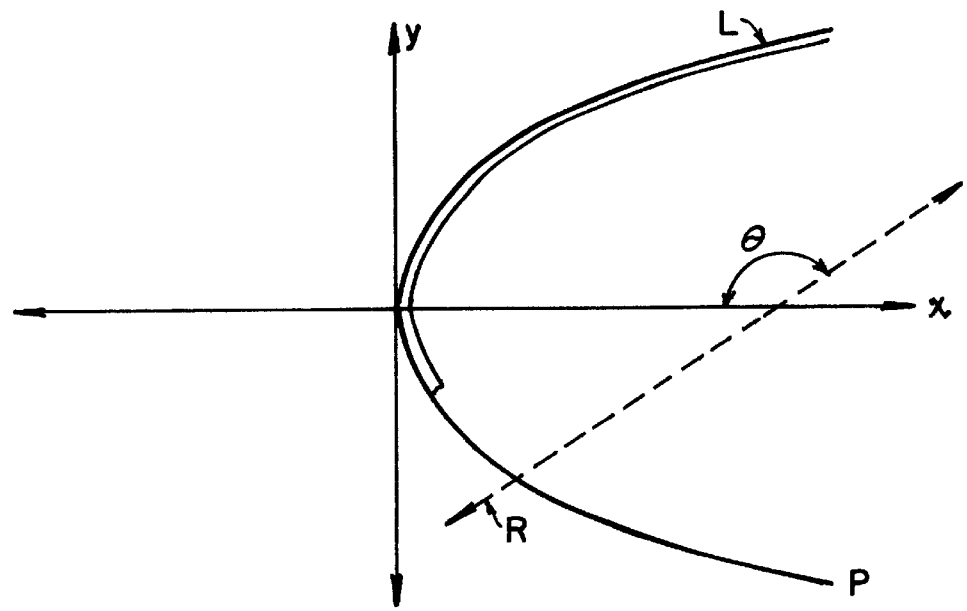
FIGS. 15 and 16 are diagrammatic views of parabolic and hyperbolic lenses, respectively, in accordance with the present invention.

Referring to FIG. 15, it is preferable that one surface of the lens L is generated by rotation of a segment of the parabola P about an axis of rotation "R", which is positioned in the same plane as the parabola at an angle of "Θ" relative to the axis of symmetry of the parabola. Referring to FIG. 8, the hyperbola H is defined by the equation:

$$y^2 = (b^2/a^2)(x^2 - a^2)$$

where "a" and "–a" are the x coordinates of the vertices V and V' of the hyperbola and $$b^2 = c^2 - a^2$$

where "c" and "–c" are the x coordinates of the foci F and F' of the hyperbola. The hyperbola H is symmetric about both the x and y axes and the center, which in this case is the origin (0,0), because both positive and negative values for y will yield a positive and negative value for x.

Figure 16:
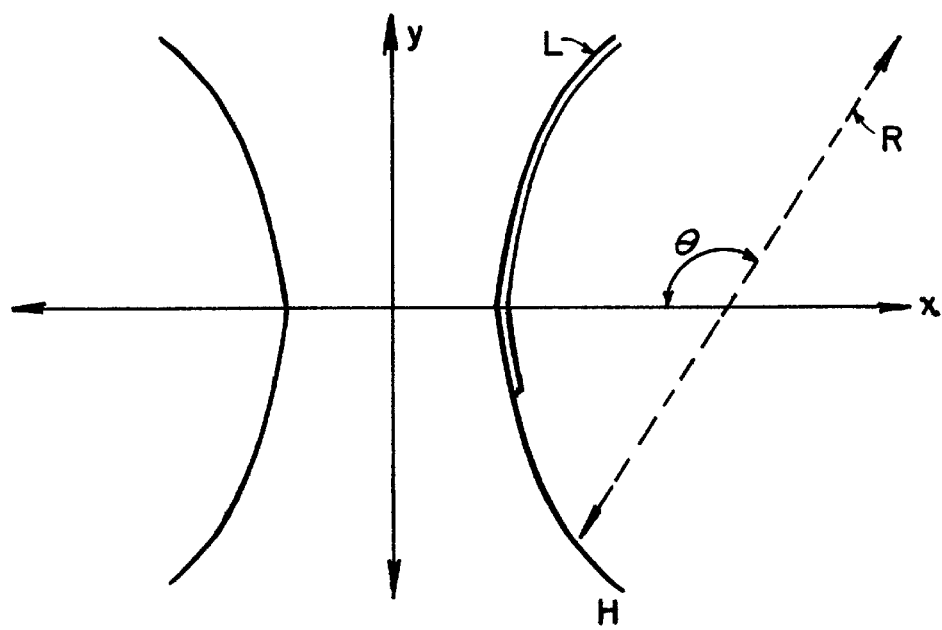

Referring to FIG. 16, it is preferable that one surface of the lens L is generated by rotation of a segment of the hyperbola H about an axis of rotation "R", which is positioned in the same plane as the hyperbola at an angle of "Θ" relative to an axis of symmetry of the hyperbola.

Figure 9:
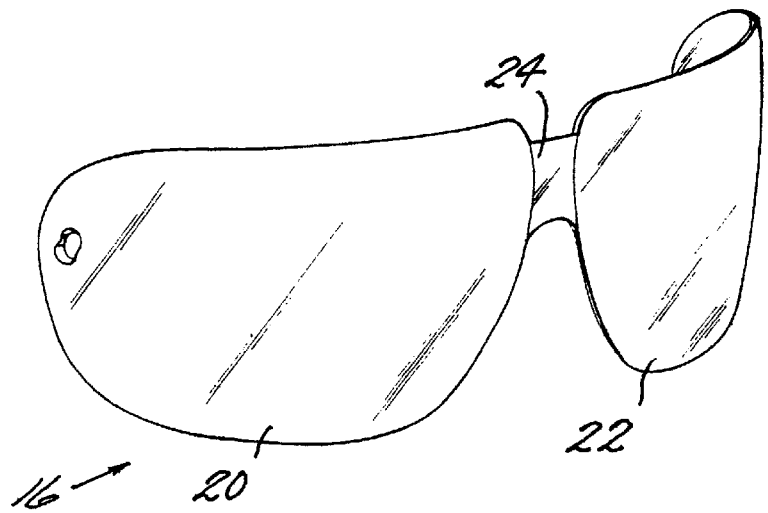
FIG. 9 is a perspective view of a parabolic piano lens of the present invention.
Figure 10:
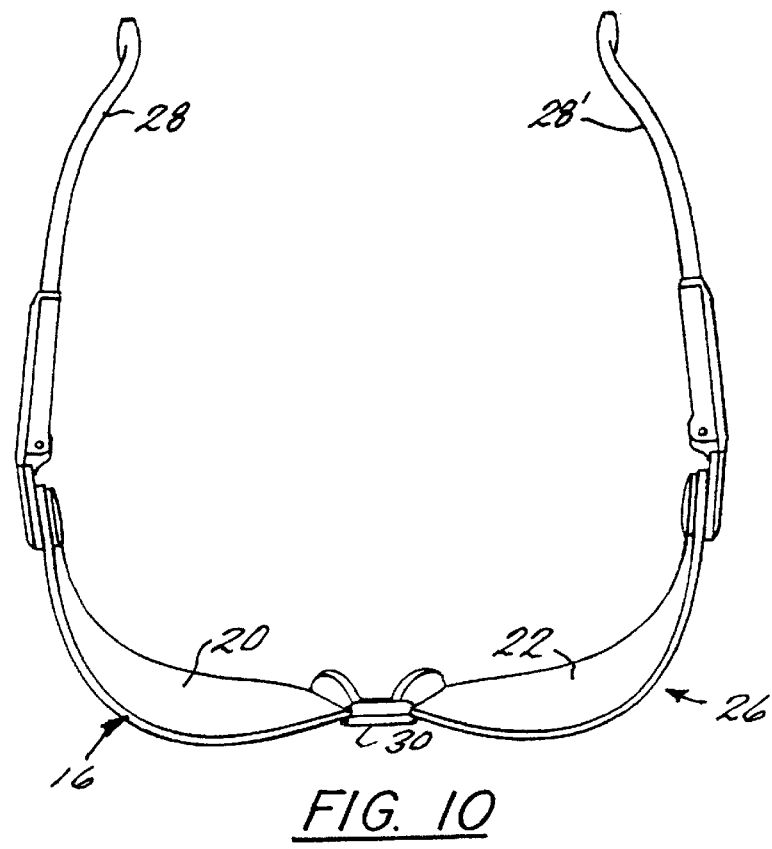
FIG. 10 is a top plan view of eyewear incorporating the parabolic plano lens in accordance with the present invention.
Figure 11:
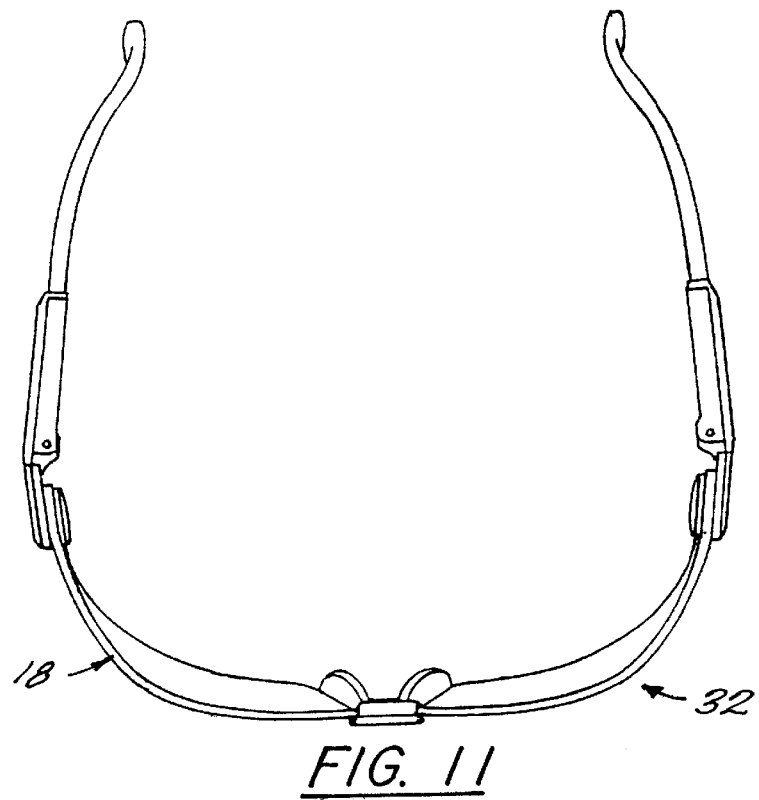
FIGS. 11 is a top plan view of eyewear incorporating the hyperbolic plano lens in accordance with the present invention.

Referring now to FIGS. 9–11, a surface (usually the front surface) of the aspheric plano lens of this invention can be formed by rotating a parabola or a hyperbola about an axis which is coplanar and offset from the axis of the parabola or hyperbola. The axis of rotation may be a parallel axis of rotation or a non parallel axis of rotation. Thus, for example, in one embodiment of this invention, the front lens surface may be formed from a section of the three dimensional shape formed by rotating a parabola or hyperbola about a base line axis. The base line is spaced from and at an angle Θ to the axis of the parabola or hyperbola and is coplanar with the axis as shown in aforementioned FIG. 15.

The other surface of the lens (usually the inner or back surface) is also preferably an aspheric shape, however typically this back surface will be a shape that differs from the front surface. The shape of the back or interior lens surface is dictated by that shape which provides zero power or plano optics to the entire lens or at least to the viewing portion of the lens, it being understood that the lateral or side portions of the lens which wrap about the wearer's face do not necessarily require zero power optics; although in many instances it is preferred that the entire lens have piano optics.

Figure 12:
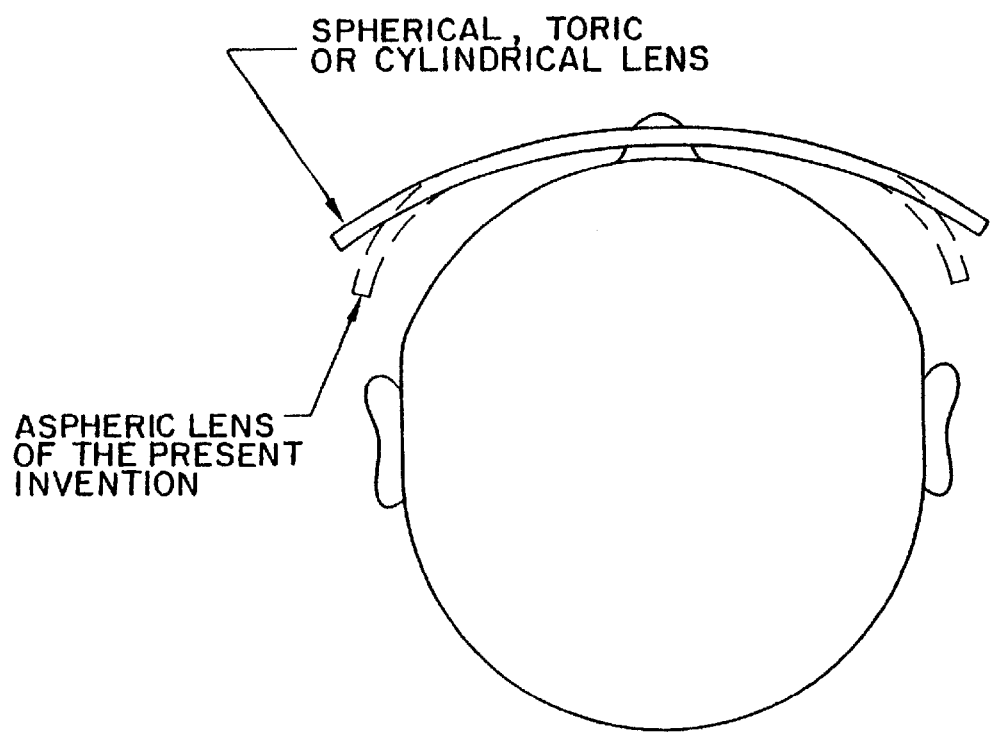
FIG. 12 is a diagrammatic top plan view comparing the aspheric piano lens of this invention to the prior art spherical, toric and cylindrical lenses of FIGS. 1–6.

Referring to FIG. 12, it is preferable to orient the parabola or hyperbola in the horizontal axis relative to the eye. The changing radius of curvature from relatively flat to progressively steeper in the horizontal meridian allows the aspheric piano lens of this invention to sufficiently wrap around the temple area as schematically shown in FIG. 12. It will be appreciated that the novel aspheric lens configuration of the present invention provides significantly greater wrap than does the spherical, toric or cylindrical lenses found in the prior art and indicated diagrammatically in FIG. 12.

Figure 13:
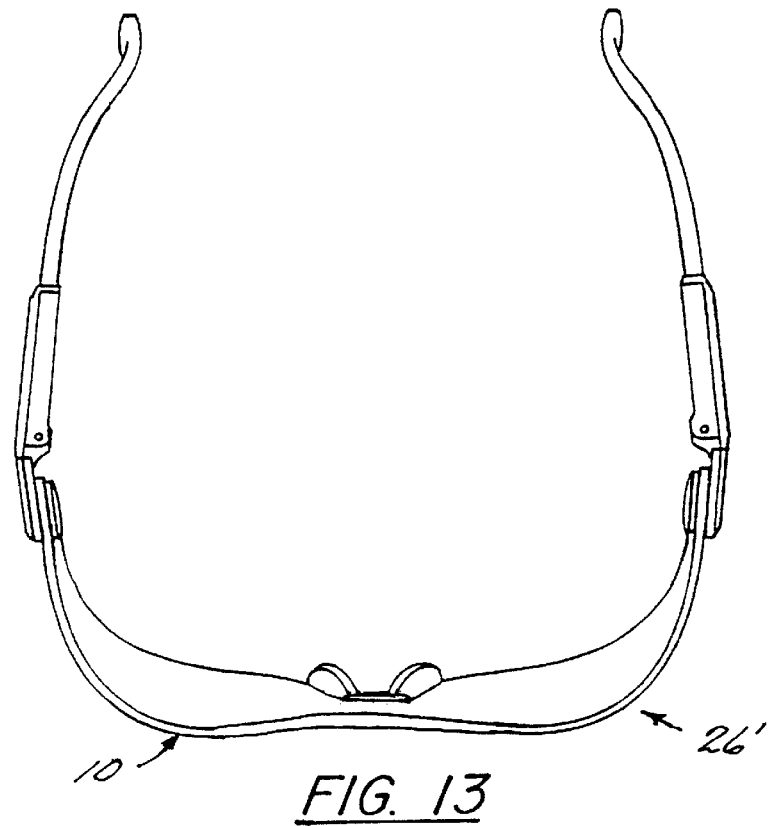
FIG. 13 is a top plan view of eyewear incorporating a continuous parabolic lens in accordance with the present invention.
Figure 14:
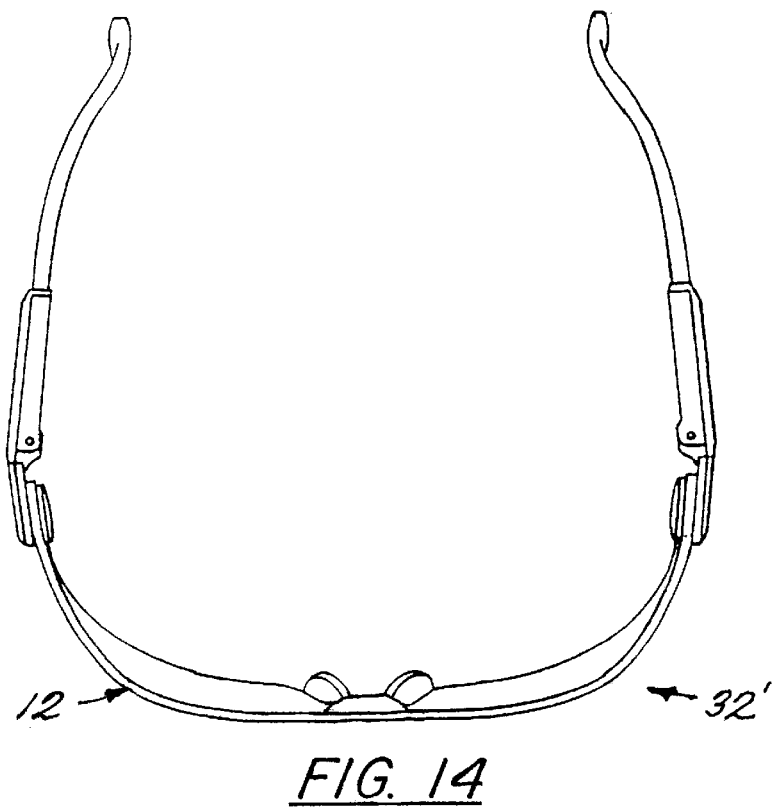
FIG. 14 is a top plan view of eyewear incorporating a continuous hyperbolic lens in accordance with the present invention.

In accordance with this invention, one large parabola or hyperbola can be used to produce a continuous lens wrapping around both temples such as shown at 10 in FIG. 13 (single parabola) and at 12 in FIG. 14 (single hyperbola) or separate parabolas or hyperbolas can be used, one for each eye, to make a dual lens for a spectacle whereby each lens provides wrap for one of the wearer's temples. A lens of this type is shown at 16 in FIGS. 9–10 for a parabola and at 18 in FIG. 11 for a hyperbola. While the separate lens portions 20 and 22 of lens 16 may be separated (and for example, interconnected by a simple frame), preferably lens portions 20 and 22 are integrally interconnected or molded by a center bar 24 to make one piece dual lenses for a spectacle as shown in FIG. 9. This same integral connection may be utilized with the hyperbola lens 18 of FIG. 11.

The lenses of this invention are preferably molded, cast or formed from a suitable optically clear material such as polycarbonate, allyl diglycol carbonate (CR-39) or glass.

Referring now to FIGS. 9, 10 and 13, lens 16 has the shape of a parabola or at least an aspheric shape having a parabolic arc. This parabolic arc is rotated about an axis spaced (offset) some distance from a given line. Preferably, the axis of rotation is coplanar with the parabola. The resulting surface of this preferred lens configuration will have a cross-section in a first axis (i.e., horizontal meridian) which is a segment of a parabola, and a cross section in a second axis (perpendicular to the first axis) which is a segment of a circle. A feature of the preferred front lens configuration is that the surface generated is rotationally symmetric. Plano lens 16 may be incorporated into eyewear such as goggles, visors, faceshields, masks, helmets and spectacles. In FIGS. 10 and 13, a pair of spectacles 26, 26' are shown having a pair of temples 28, 28' and an optional nosepiece 30 as described in detail in aforementioned U.S. Pat. No. 5,825,455.

Referring now to FIGS. 11 and 14, lens 18 is based on a hyperbola or at least an aspheric shape having a hyperbolic arc. The hyperbola is preferably rotated about an axis spaced from and coplanar with the hyperbola. The resulting surface of this lens configuration 18 will have a cross-section in a first axis which is a segment of a hyperbola, and a cross-section in a second axis (perpendicular to the first axis) which is a segment of a circle. Again, a feature of this preferred lens configuration is that the surface generated is rotationally symmetric. Like piano lens 16, plano lens 18 may be incorporated into eyewear such as goggles, visors, faceshields, masks, helmets and spectacles. In FIGS. 11 and 14, a pair of spectacles 32, 32' are shown having a pair of temples 28, 28' and an optional nosepiece 30 as described hereinabove.

Preferably, the front surfaces of the lenses in FIGS. 9–11 and 12–13 have either a parabolic or hyperbolic surface while the back surface curvature is designed to provide zero power for straight ahead gaze at a pupillary distance. This back surface is formed in the manner described in aforementioned U.S Pat. No. 5,825,455 wherein the thickness between the front and back surfaces of the lens are varied to achieve the piano optics in at least the viewing portion of the lens.

As shown in detail in U.S. Pat. No. 5,825,455, the eyewear of FIGS. 9–11 and 13–14 may include a frame completely or partially surrounding the lenses. In addition, a foam flange may be incorporated about some or all of the periphery of the lenses as disclosed in U.S. Pat. No. 5,825, 455.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A lens comprising:

a first surface and a second surface spaced from said first surface, said lens further having a viewing portion;

said first surface comprising a section of a 3-dimensional surface which is defined by rotating a parabolic shape about an axis, which axis is not an axis of said parabolic shape, and which is offset from an axis of said parabolic shape; and said second surface having a curvature which, together with said first surface, provides zero power to at least said viewing portion of said lens.

2. The lens of claim 1 wherein:

said parabolic shape includes a parabolic arc.

3. The lens of claim 2 wherein:

said parabolic shape comprises a parabola.

4. The lens of claim 3 wherein:

said offset axis is coplanar with said parabolic shape.

5. The lens of claim 4 wherein:

said offset axis is infinitely distanced from said axis of said parabolic shape.

6. The lens of claim 1 wherein:

said lens comprises dual lens sections.

7. The lens of claim 6 wherein:

said dual lens sections are interconnected by a bar.

8. The lens of claim 1 wherein:

said lens is comprised of formed polymeric material.

9. The lens of claim 1 wherein:

said offset axis is at an angle e relative to an axis of said parabolic shape.

10. Eyewear comprising:

a lens having a first surface and a second surface spaced from the first surface, said lens further having a viewing portion;

said first surface comprising a section of a 3-dimensional surface defined by rotating a parabola shape about an axis, which axis is not an axis of said parabola shape, and which is offset from an axis of the parabola shape;

said second surface having a curvature which, together with said first surface, provides plano optics to at least said viewing portion; and a support structure for positioning said lens at a location spaced from the eyes of the wearer.

11. The eyewear of claim 10 wherein said eyewear comprises spectacles.

12. The eyewear of claim 10 wherein:

said lens comprises dual lens sections, one lens section being associated with each eye of a wearer.

13. The eyewear of claim 12 wherein:

said dual lens sections are interconnected by an integral bar.

14. The eyewear of claim 10 wherein:

said lens comprises a continuous lens for wrapping about both temples of a wearer.

15. The eyewear of claim 10 wherein:

said piano optics is further provided by varying the thickness between said spaced first and second surfaces of said lens.

16. The eyewear of claim 10 wherein:

the entirety of said lens has plano optics.

17. The eyewear of claim 10 wherein:

said lens is comprised of formed plastic material.

18. The eyewear of claim 11 wherein:

said spectacles include a pair of temples.

19. The eyewear of claim 11 wherein:

said spectacle include a nose bridge.

20. The eyewear of claim 18 wherein:

said spectacles include a nose bridge.

21. The eyewear of claim 10 including:

a frame at least partially surrounding said lens.

22. The eyewear of claim 21 wherein:

said frame fully surrounds said lens.

23. The eyewear of claim 10 wherein:

said eyewear is selected from the group consisting of visors, goggles, masks and helmets.

24. The eyewear of claim 10 wherein:

said offset axis is at an angle $\ominus$ relative to an axis of said parabolic shape.

25. A lens comprising:

a first surface and a second surface spaced from said first surface, said lens further having a viewing portion;

said first surface comprising a section of a 3-dimensional surface which is defined by rotating a hyperbolic shape about an axis, which axis is not an axis of said hyperbolic shape, and which is offset from an axis of said hyperbolic shape; and said second surface having a curvature which, together with said first surface, provides zero power to at least said viewing portion of said lens.

26. The lens of claim 25 wherein:

said hyperbolic shape includes a hyperbolic arc.

27. The lens of claim 26 wherein:

said hyperbolic shape comprises a hyperbola.

28. The lens of claim 27 wherein:
said offset axis is coplanar with said hyperbolic shape.

29. The lens of claim 28 wherein:
said offset axis is infinitely distanced from said axis of said hyperbolic shape.

30. The lens of claim 25 wherein:
said lens comprises dual lens sections.

31. The lens of claim 30 wherein:
said dual lens sections are interconnected by a bar.

32. The lens of claim 25 wherein:
said lens is comprised of formed polymeric material.

33. The lens of claim 25 wherein:
said offset axis is at an angle $\ominus$ relative to an axis of said hyperbolic shape.

34. Eyewear comprising:
a lens having a first surface and a second surface spaced from the first surface, said lens further having a viewing portion;
said first surface comprising a section of a 3-dimensional surface defined by rotating a hyperbola shape about an axis, which axis is not an axis of said hyperbola shape, and which is offset from an axis of the hyperbola shape;
said second surface having a curvature which, together with said first surface, provides plano optics to at least said viewing portion; and
a support structure for positioning said lens at a location spaced from the eyes of the wearer.

35. The eyewear of claim 34 wherein said eyewear comprises spectacles.

36. The eyewear of claim 34 wherein:
said lens comprises dual lens sections, one lens section being associated with each eye of a wearer.

37. The eyewear of claim 36 wherein:
said dual lens sections are interconnected by an integral bar.

38. The eyewear of claim 34 wherein:
said lens comprises a continuous lens for wrapping about both temples of a wearer.

39. The eyewear of claim 34 wherein:
said piano optics is further provided by varying the thickness between said spaced first and second surfaces of said lens.

40. The eyewear of claim 34 wherein:
the entirety of said lens has plano optics.

41. The eyewear of claim 34 wherein:
said lens is comprised of formed plastic material.

42. The eyewear of claim 35 wherein:
said spectacles include a pair of temples.

43. The eyewear of claim 35 wherein:
said spectacles include a nose bridge.

44. The eyewear of claim 42 wherein:
said spectacles include a nose bridge.

45. The eyewear of claim 34 including:
a frame at least partially surrounding said lens.

46. The eyewear of claim 45 wherein:
said frame fully surrounds said lens.

47. The eyewear of claim 34 wherein:
said eyewear is selected from the group consisting of visors, goggles, masks and helmets.

48. The eyewear of claim 34 wherein:
said offset axis is at an angle $\ominus$ relative to an axis of said hyperbolic shape.

* * * * *

UNITED STATES PATENT AND TRADEMARK OFFICE
CERTIFICATE OF CORRECTION

PATENT NO.    : 6,254,236 B1
DATED         : July 3, 2001
INVENTOR(S)   : Fecteau et al.

It is certified that error appears in the above-identified patent and that said Letters Patent is hereby corrected as shown below:

Column 1,
Line 58, after "equal to" insert therefor -- $\infty$ --

Column 2,
Line 4, before "safety eyewear" delete "piano" and insert therefor -- plano --

Column 4,
Line 26, after "aspheric" delete "piano" and insert therefor -- plano --
Line 59, after "parabolic" delete "piano" and insert therefor -- plano --

Column 5,
Line 2, after "aspheric" delete "piano" and insert therefor -- plano --
Line 27, after "aspheric" delete "piano" and insert therefor -- plano --

Column 6,
Line 20, after "have" delete "piano" and insert therefor -- plano --

Column 7,
Line 8, after "Like" delete "piano" and insert therefor -- plano --
Line 21, after "achieve the" delete "piano" and insert therefor -- plano --
Line 66, after "angle" delete "e" and insert therefor -- $\theta$ --

Column 8,
Line 27, after "said" delete "piano" and insert therefor -- plano --
Line 38, after "said" delete "spectacle" and insert therefor -- spectacles --

UNITED STATES PATENT AND TRADEMARK OFFICE
CERTIFICATE OF CORRECTION

PATENT NO.    : 6,254,236 B1
DATED         : July 3, 2001
INVENTOR(S)   : Fecteau et al.

It is certified that error appears in the above-identified patent and that said Letters Patent is hereby corrected as shown below:

Column 10,
Line 8, after "said" delete "piano" and insert therefor -- plano --

Signed and Sealed this

Eleventh Day of January, 2005

JON W. DUDAS
*Director of the United States Patent and Trademark Office*